(12) United States Patent
Kasem

(10) Patent No.: US 10,603,139 B2
(45) Date of Patent: Mar. 31, 2020

(54) ANGULATED TRANSFERS FOR DENTAL IMPLANTS

(71) Applicant: Yahya Kasem, Mokeibleh Village (IL)

(72) Inventor: Yahya Kasem, Mokeibleh Village (IL)

( * ) Notice: Subject to any disclaimer, the term of this patent is extended or adjusted under 35 U.S.C. 154(b) by 0 days.

(21) Appl. No.: 15/364,289

(22) Filed: Nov. 30, 2016

(65) Prior Publication Data
US 2017/0239019 A1 Aug. 24, 2017

(30) Foreign Application Priority Data
Feb. 18, 2016 (IL) .......................................... 244188

(51) Int. Cl.
*A61C 8/00* (2006.01)
*A61C 9/00* (2006.01)
(52) U.S. Cl.
CPC ............ *A61C 8/0001* (2013.01); *A61C 8/006* (2013.01); *A61C 8/0056* (2013.01); *A61C 8/0068* (2013.01); *A61C 9/00* (2013.01)
(58) Field of Classification Search
CPC ... A61C 8/0001; A61C 8/0056; A61C 8/0068; A61C 9/00
See application file for complete search history.

(56) References Cited

U.S. PATENT DOCUMENTS

| | | | |
|---|---|---|---|
| 4,988,297 A | 1/1991 | Lazzara et al. | |
| 5,135,395 A | 8/1992 | Marlin | |
| 6,332,777 B1 | 12/2001 | Sutter | |
| 2003/0082498 A1* | 5/2003 | Halldin | A61C 8/0001 433/173 |
| 2011/0229850 A1* | 9/2011 | Bretton | A61C 8/0001 433/172 |
| 2013/0084541 A1 | 4/2013 | von Malottki | |
| 2014/0147812 A1 | 5/2014 | Ilter et al. | |

FOREIGN PATENT DOCUMENTS

| | | |
|---|---|---|
| WO | 199629019 | 9/1996 |
| WO | 2003030768 | 4/2003 |
| WO | 2010075993 | 7/2010 |
| WO | 2012065848 | 5/2012 |
| WO | 2015189648 | 12/2015 |
| WO | WO 2015/189648 A2 * | 12/2015 |

OTHER PUBLICATIONS

International Search Report for application PCT/IB2016/057205 dated Mar. 16, 2017.
Supplementary Partial European Search Report for corresponding EP application 16 89 0424 dated Jan. 25, 2019.

* cited by examiner

*Primary Examiner* — Ralph A Lewis
(74) *Attorney, Agent, or Firm* — Heidi Brun Associates Ltd.

(57) ABSTRACT

A system to transfer the location of at least one tilted dental implant to an impression material, the system includes an angulated component connectable to a tilted dental implant and a cap to snap onto the angulated component. The system provides a tilt, a location and a rotation of the tilted dental implant into the impression material.

8 Claims, 13 Drawing Sheets

ANGULATED TRANSFERS FOR DENTAL IMPLANTS

CROSS REFERENCE TO RELATED APPLICATIONS

This application claims priority from Israeli patent application 244188, filed Feb. 18, 2016 which is incorporated herein by reference.

FIELD OF THE INVENTION

The present invention relates to techniques for transferring the location, angulation and degree of rotation (i.e. "timing") of dental implants from the mouth to a plaster model generally, and to such techniques for tilted implants in particular.

BACKGROUND OF THE INVENTION

Rehabilitation of a mouth and restoration of missing teeth using dental implants and dental prostheses are known. A dental implant is a surgical component that interfaces with the bone to support a dental prosthesis such as a crown, bridge, denture, facial prosthesis or to act as an orthodontic anchor. The dental implants are made of materials, such as titanium, that can form an intimate bond to bone. The implant is first implanted in the bone of the jaw, after which a dental prosthesis is added. Dental implants in the bone are used as an anchorage, support and retention for the different dental prostheses.

Many types of implants exist, each with a different design, size and connection element. The connection element of an implant is used to connect the prostheses to the implant directly or indirectly. Different connection elements may be found in different implants. The prostheses may be directly screwed to the implant, or alternatively it may be screwed or cemented to another prosthetic component connected to the implant.

Each prosthesis must fit to specific needs and thus must be precise and must fit exactly to the specific implant. In order to ensure the accuracy of the manufactured prosthesis, it is of great importance to transfer the exact location, angulation and degree of rotation (i.e. "timing") of dental implants from the patient's mouth to the plaster model.

In order to create the dental prosthesis, an impression of the jaw, having the location and angulation of the dental implants (and any existing teeth), is created by the physician in the clinic. This impression is used later to create the plaster model from which the prosthesis is fabricated in the laboratory.

A common technique for taking an impression of the mouth is the closed tray technique, as described in FIGS. 1-5, to which reference is now made. FIG. 1 schematically illustrates a dental arch with two straight implants 14, implanted into bone 10, below gingiva 12.

In order to fabricate an accurate model, it is crucial to copy the exact location of the implants, the teeth and any soft tissue around and between the implants and the teeth. In particular, it is of great importance to copy the exact location, angulation and rotation (called "timing" in the professional terminology) of the dental implants. In one commonly used technique to copy the exact location, angulation and timing of implants 14, metal components 16 are screwed into each implant 14 and a plastic cap 18 is snapped onto metal component 16. As a result, metal components 16 protrude above bone 10 and gingiva 12. The combined plastic cap 18 and metal component 16 is known as a "transfer" element.

FIG. 2 shows plastic caps 18 snapped onto each metal component 16. FIG. 2 also shows an impression material 22, made of an elastomeric material, placed in an impression tray 20, to be pressed over the structures to be copied in the mouth (FIG. 3). As can be seen, elastomeric impression material 22 surrounds plastic caps 18. When elastomeric impression material 22 hardens, it becomes rigid, trapping plastic caps 18 therein.

After elastomeric impression material 22 has hardened, the dentist releases it from the mouth, as illustrated in FIG. 4. Released impression material 22 contains plastic caps 18 loosened from metal components 16 to which they were connected. Impression material 22 thus has the exact shape of the dental arch, which includes the shape of gingiva 12 and the shape and location of any existing teeth (not shown in the figures for simplicity), as well as the exact location, angulation and timing of each implant 14, as indicated by plastic caps 18.

As shown in FIG. 5, after removing impression material 22, metal components 16 are unscrewed from dental implants 14. Removed metal components 16 are then screwed into implant analogs 54 which have the same connection type as the implants that remain in the patient's mouth, and the resultant structures, built of removed metal components 16, and implant analogs 54, are snapped into plastic caps 18 immersed in rigid impression material 22. The resultant structure is ready to be used for standard fabrication of a dental plaster model in the dental laboratory. Implant analogs 54 may have any suitable shape and structure, as is known.

SUMMARY OF THE PRESENT INVENTION

There is provided, in accordance with a preferred embodiment of the present invention, a system to transfer at least a location of at least one tilted dental implant to an impression material, the system includes an angulated component connectable to a tilted dental implant; and a cap to snap onto the angulated component. The system provides a tilt, a location and a rotation of the tilted dental implant into the impression material.

Additionally, there is provided, in accordance with a preferred embodiment of the present invention, a system for releasing a dental impression from at least one tilted dental implant, the system includes an angulated component, connectable to the tilted dental implant, to straighten the release path of the impression from the tilted implant; and a cap to snap onto the angulated component and to be released from the angulated component into the impression.

Furthermore, there is provided in accordance with a preferred embodiment of the present invention, an angulated component including a prosthesis placeholder; a connector to connect to a tilted dental implant; and a base between the connector and the prosthesis placeholder, where the prosthesis placeholder and the base provides an angle between the connector and the prosthesis placeholder, the angle being similar to a tilt angle of the tilted dental implant with respect to the perpendicular axis of the occlusal plane.

Still further, in accordance with a preferred embodiment of the present invention, the base is a wedged base having an angle similar to the tilt angle.

Moreover, in accordance with a preferred embodiment of the present the prosthesis placeholder is connected to the base at an angle similar to said tilt angle.

Additionally, in accordance with a preferred embodiment of the present invention, the connector matches the shape of a connector of the implant.

Further, in accordance with a preferred embodiment of the present invention, the connector has the shape of an equilateral polygon.

Still further, in accordance with a preferred embodiment of the present invention, the prosthesis placeholder comprises an anti-rotation element to keep a rotational position of the cap fixed in order to match a rotational location of the dental implant.

Still further, in accordance with a preferred embodiment of the present invention, the connector comprises a screw.

Still further, in accordance with a preferred embodiment of the present invention, the angulated component is one of: a permanent prosthetic element and a temporary prosthetic element.

There is also provided, in accordance with a preferred embodiment of the present invention, a method for transferring a location, an angulation and a rotation of a tilted implant from a mouth to a model using an impression material, the method includes attaching an angulated element to a tilted implant to straighten a release path for the impression material; snapping a cap to the angulated element; placing the impression material onto the mouth; and removing the impression material from the mouth along with the cap.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
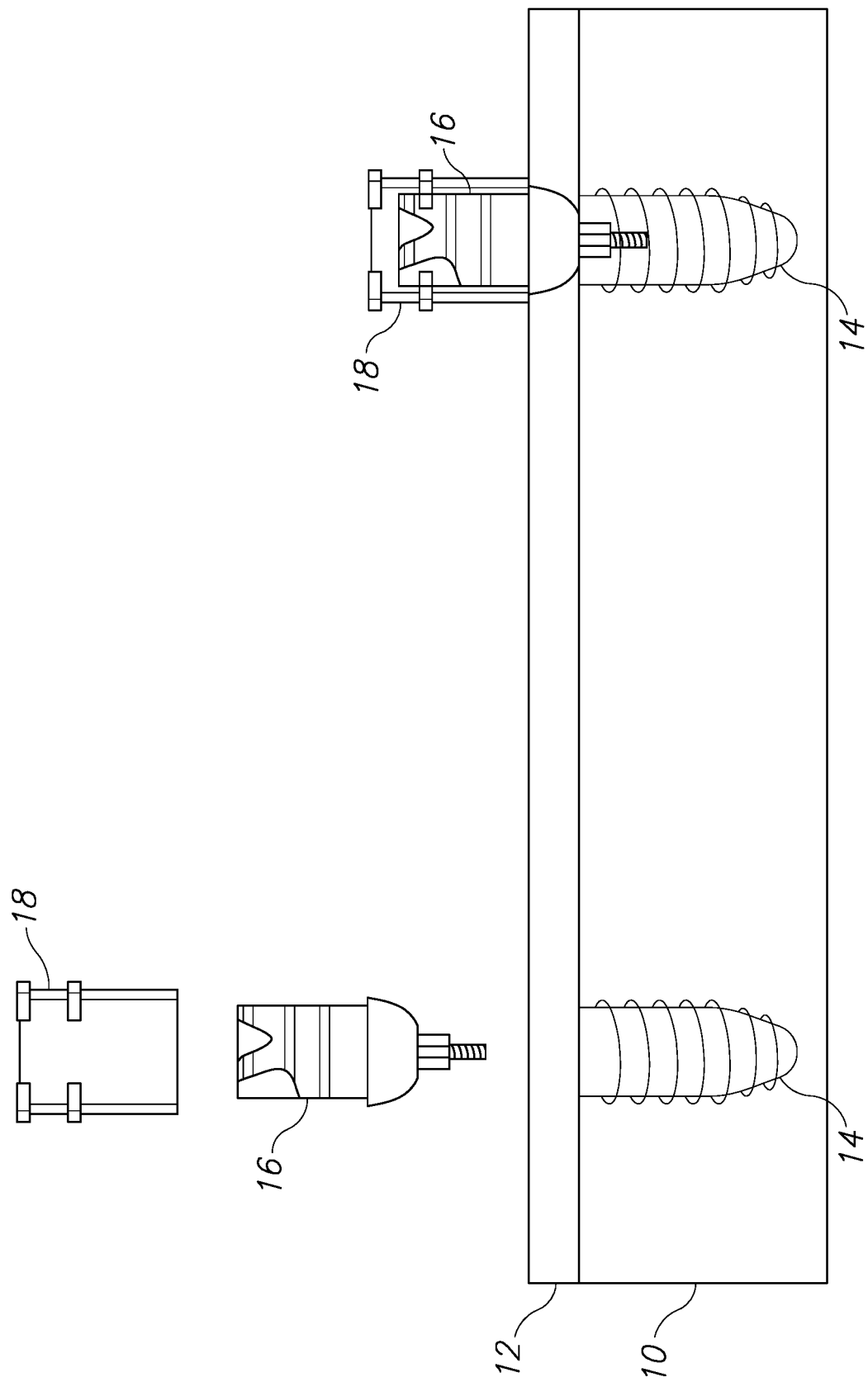
FIGS. 1, 2, 3, 4 and 5 are schematic illustrations of the procedure of transferring the location, angulation and timing of straight implants.
Figure 2:
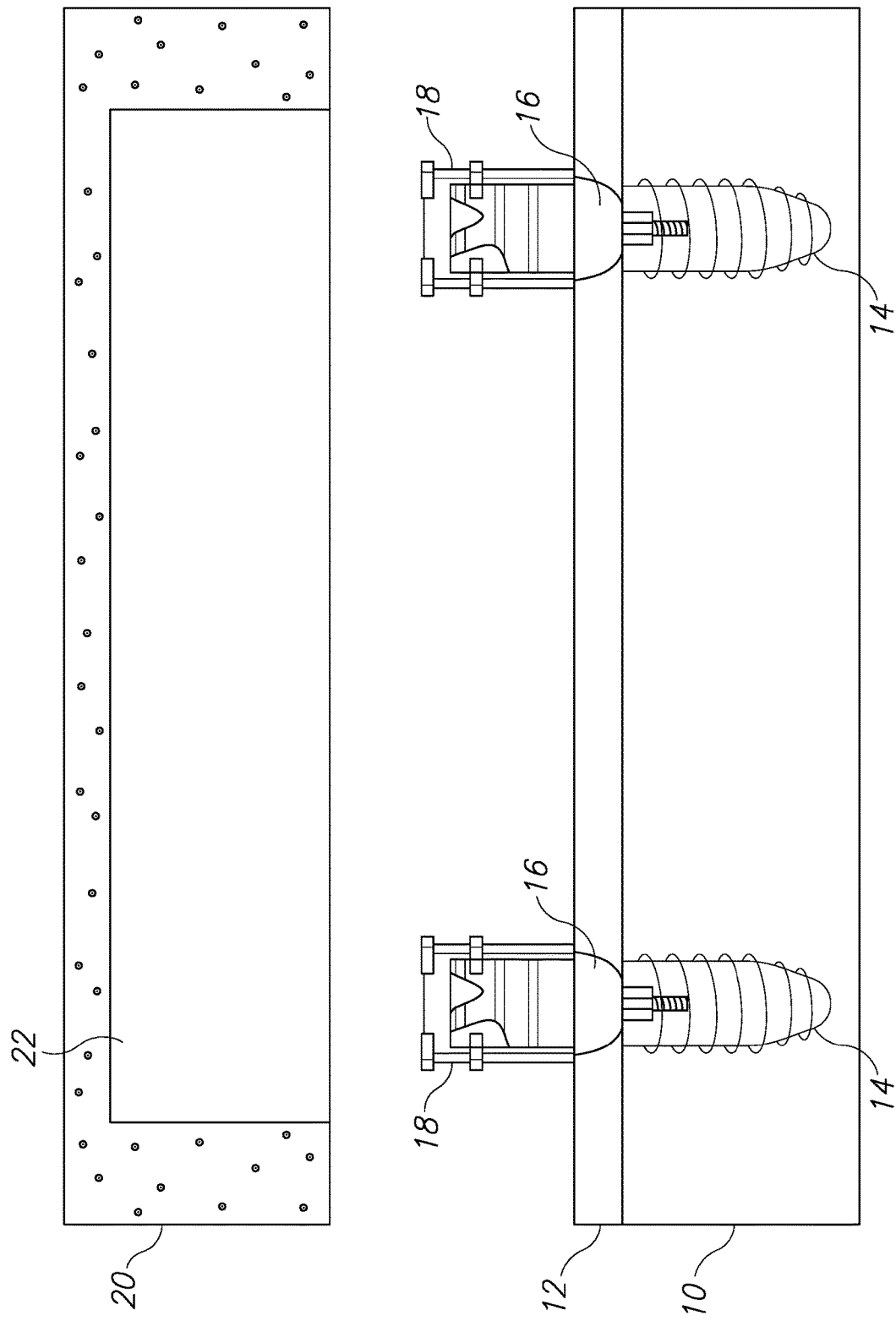
Figure 3:
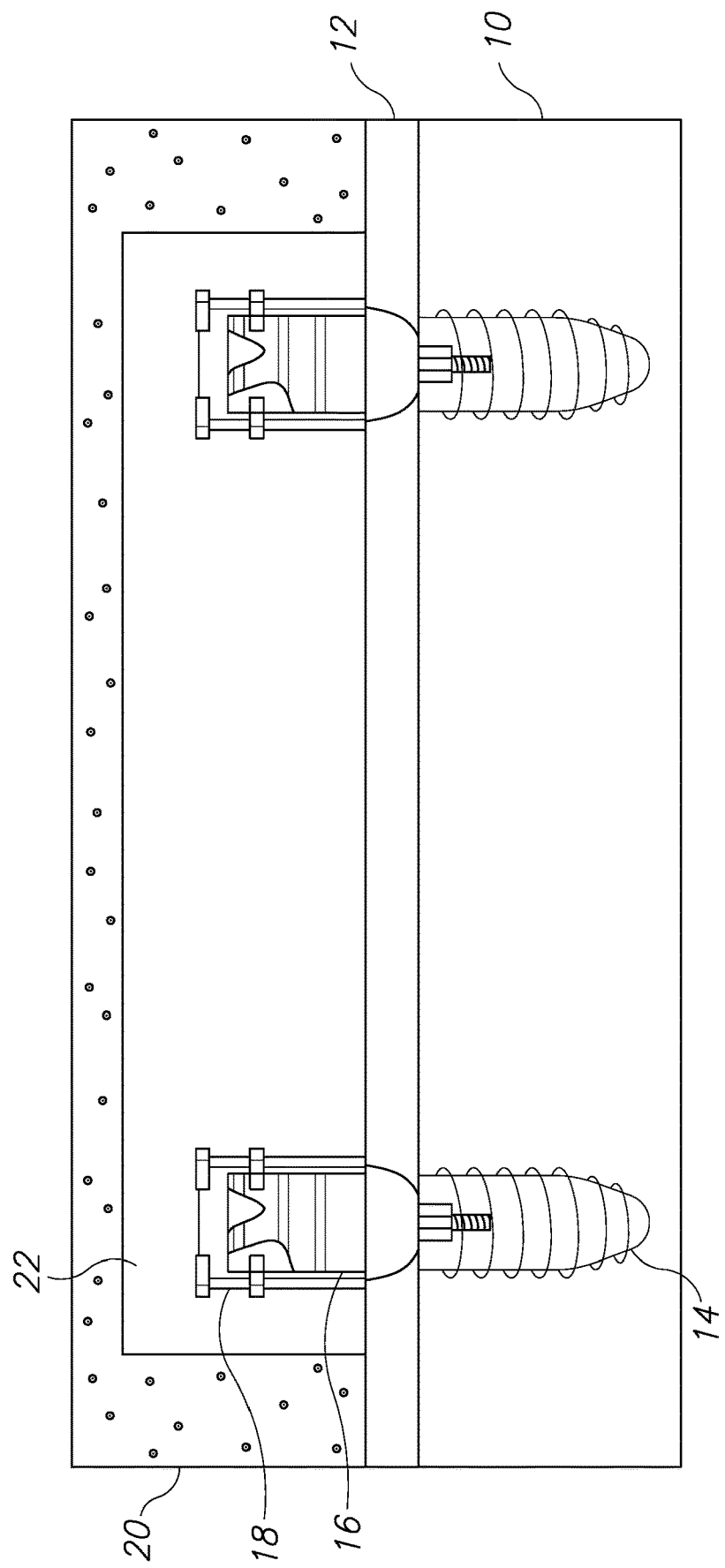
Figure 4:
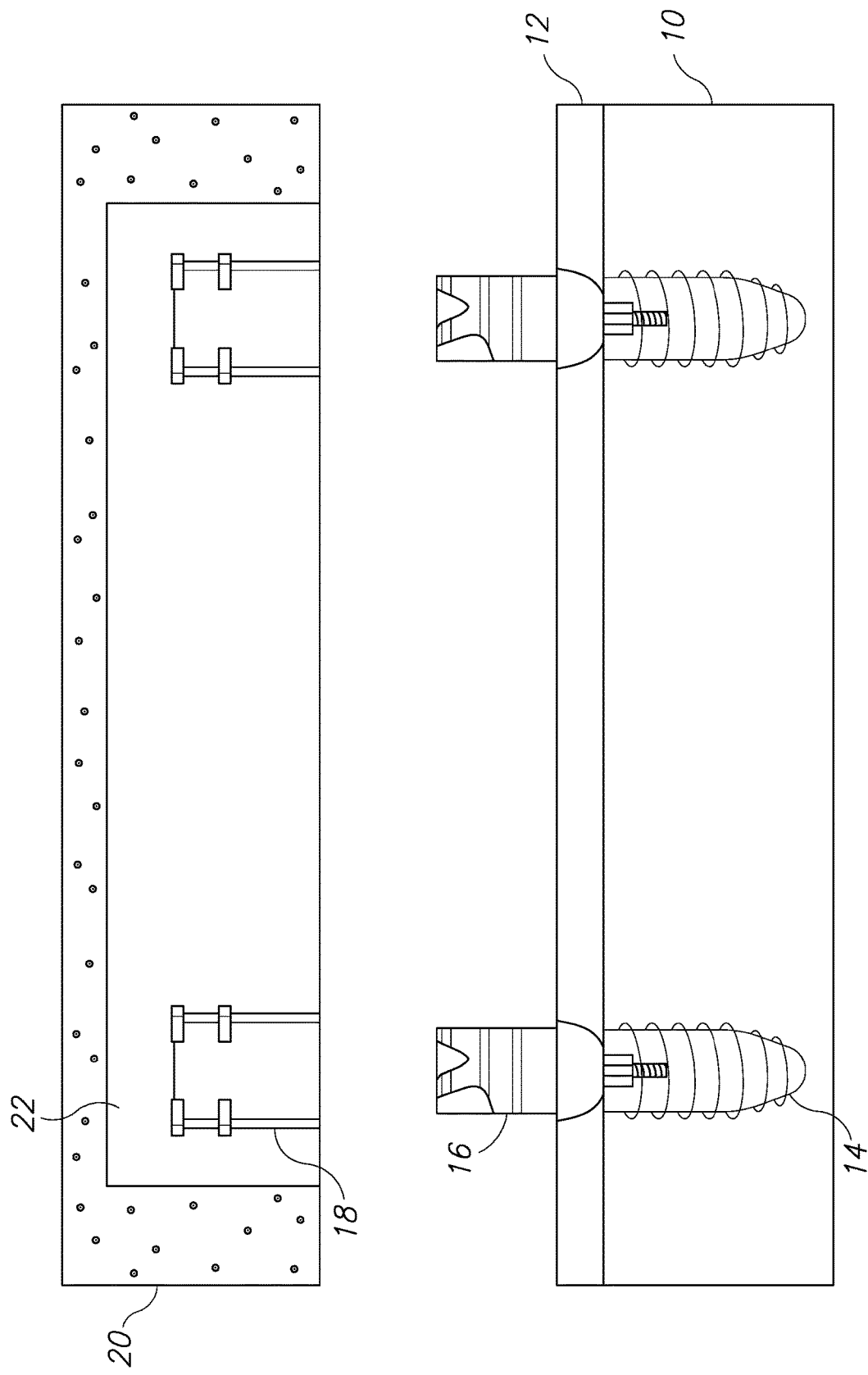

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicant has realized that copying the location and angulation of dental implants using the closed tray technique described hereinabove is simple and accurate enough for straight implants (i.e. when the axis of the implant is the same as the axis of the retrieval path of the impression from mouth) but may be inadequate when the implant is tilted (the axis of the implant is not parallel to the retrieval path of the impression from mouth).

Tilted implants may be needed in several cases. For example, when the patient does not have enough bone for placing the implant in the specific site needed, the implant tip can be slightly tilted keeping the connection element in the site needed but tilted.

Figure 6:
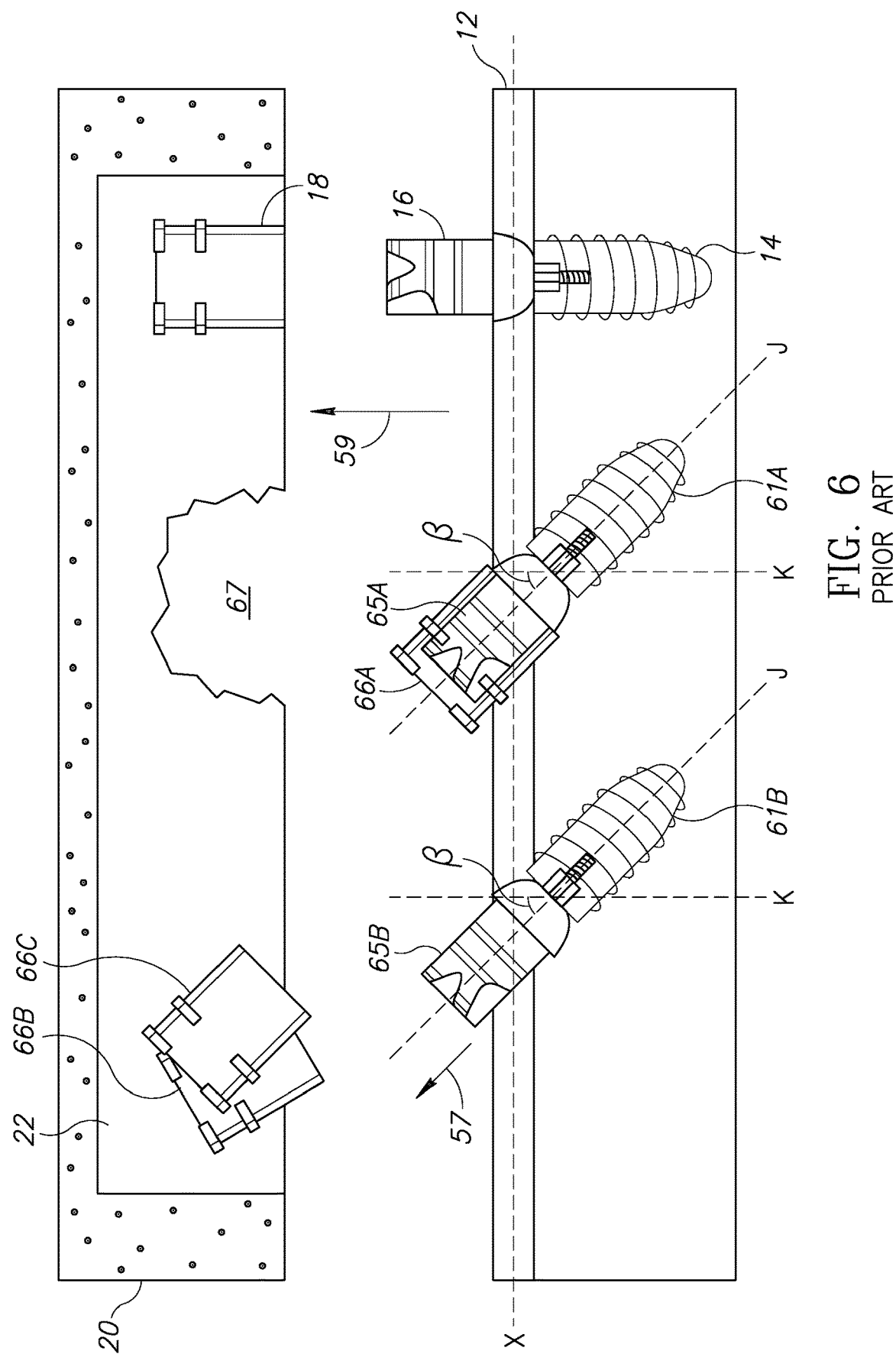
FIG. 6 is a schematic illustration of the problems of the standard procedure when the implants are tilted.

This tilt can also be used, for example, to avoid an injury to anatomical structures, such as an adjacent nerve canal (usually in the lower jaw) or the maxillary sinus. FIG. 6, to which reference is now made, illustrates three implants; implant 14 is a straight implant while implants 61A and 61B are tilted implants (i.e. there is an angle $\beta$ between an axis j of dental implants 61A and 61B, located in the patient mouth, and an axis k which is perpendicular to the occlusal plane x and represents the direction of releasing the impression tray from the mouth in the closed tray technique.

Using the closed tray technique, described hereinabove, plastic cap 18, immersed in impression material 22, indicates the exact location, angulation and timing of straight dental implant 14. Plastic cap 18 can be easily released from metal component 16 to which it was snapped. However, impression material 22 has no accurate indication of the exact locations and angulations of tilted dental implants 61A and 61B.

For tilted dental implant 61A, there is no indication at all in impression material 22 regarding its location and angulation, as plastic cap 66A was not released from metal component 65A, to which it was attached. Moreover, during the release process, impression material 22 in area 67 was damaged by plastic cap 66 which remained attached to metal component 65.

For tilted dental implant 61B, plastic cap 66B was successfully released from metal component 65B. However, plastic cap 66B changed its location within elastomeric material 22 during the release process. Typically, it moves horizontally within elastomeric material 22 before being retrieved, and as a result, the location and angulation of tilted dental implant 66B in elastomeric impression material 22 is not accurate. In FIG. 6, the area labeled 66C, represents the accurate location and angulation where plastic cap 66B should have been, if it hadn't moved during its release from metal component 65B.

It will be appreciated that the release path 59 of plastic cap 18 (related to straight implant 14) is parallel to the release path of the impression tray from the mouth (usually perpendicular to the occlusal plane) while the release path of plastic cap 66A or 66C (related to tilted implant 61A or 61B) is not parallel to the release path of the impression tray.

Applicant has realized that when an implant is angulated, it is very difficult to transfer the exact location and angulation of the tilted implant to the plaster model using the closed tray technique. For tilted implants, the removal of the impression tray from the mouth requires more force. The result may be either a damaged impression material or an inaccurate implant location and angulation indication of the implant in the impression material.

Applicant has realized that when the plaster model is not accurate, the laboratory technician cannot create a precise dental prosthesis and the inaccurate dental prosthesis may need to be fixed during additional dental sessions with the patient. The prosthesis repair procedure may be long, painful and expensive and may result with an inferior final result.

FIGS. 7A, 7B, 7C and 7D to which reference is now made, illustrates a preferred embodiment of an angulated transfer 70, constructed and operative according to a preferred embodiment of the present invention. Angulated transfer 70 comprises a metal component 71 and a plastic cap 72.

Metal component 71 comprises a prosthesis placeholder 73, a screw 76 for connecting metal component 71 to tilted dental implant 61, and a base 74 between prosthesis placeholder 73 and screw 76.

Base 74 comprises a wedge 741 (FIG. 7A) having an upper platform 742 and a connector 745. Upper platform 742 may be at an angle α to an axis 701 of the implant. Angle α may complement angle β (FIG. 6) to 90° such that when metal component 71 is screwed into a tilted implant, such as tilted implant 61, prosthesis placeholder 73 may be generally perpendicular to occlusal plane x. Angulated transfers 70 may be made with different values of angle β, so that a dentist may select the appropriate one according to the angulation (the angles β) of the dental implants of a patient. The value of angle β generally used may be between 10°-45°, for example, 15°, 25°, 30°, and 45° but can be fabricated in any angle desired according to the tilt of the implant.

Connector 745 (FIG. 7D) may be used for attaching metal component 71 to dental implant 61. The cross section of connector 745 may have the shape of a hexagon, an octagon or any other equilateral polygon to fit the given shape of the dental implant connection type implanted in the patient's jaw. Different implants, from different vendors may have different inner or outer shapes to which connector 745 may be connected, and connector 745 may be manufactured in the possible supported shapes. The "timing" may be achieved by preserving the single specific spatial insertion location of metal component 71 in plastic cap 72 determined by the implant connection that limits the degree of rotation of the analog around its long axis to only 6 identical rotation degrees (when the implant has a hexagon connection) or only 8 identical rotation degrees (when implant with octagon connection is used)

A screw access hole 731 (FIG. 7D) may lie within prosthesis placeholder 73, and may give access to screw 76.

An anti-rotation flat surface 732 may also be formed within prosthesis placeholder 73. Anti-rotation surface may maintain the definitive adaptation of plastic cap 72 against metal component 71, and may prevent rotation of plastic cap 72 around metal component 71. Rotation surface 732 may preserve the "timing" (or rotation angle) of the implant in the plaster model.

One or more retention grooves 735 (FIGS. 7B and 7C) may be present on metal component 71. The purpose of retention grooves 735 is to enable plastic cap 72 to snap onto metal component 71.

Plastic cap 72 may comprise one or more protrusions 751 on an external surface 753 and an anti-rotation protrusion 752 and one or more retention ridges 755 on an internal surface 754.

Protrusions 751 on the outer surface of plastic cap 72 may keep plastic cap 72 stuck in impression material 22 when released from the mouth.

Anti-rotation protrusion 752 on inner surface of plastic cap 72 may serve to indicate the rotation of metal component 71 in space (its "timing") with respect to tilted dental implant 61. While stuck in impression material 22, the rotation of anti-rotation protrusion 752 may determine the "timing" of a metal component, similar to component 71, that is snapped into it during the process of creating the plaster model.

Retention ridges 755 may be used to snap plastic cap 72 into grooves 735, thereby snapping plastic cap 72 to metal element 71.

Figure 7A:
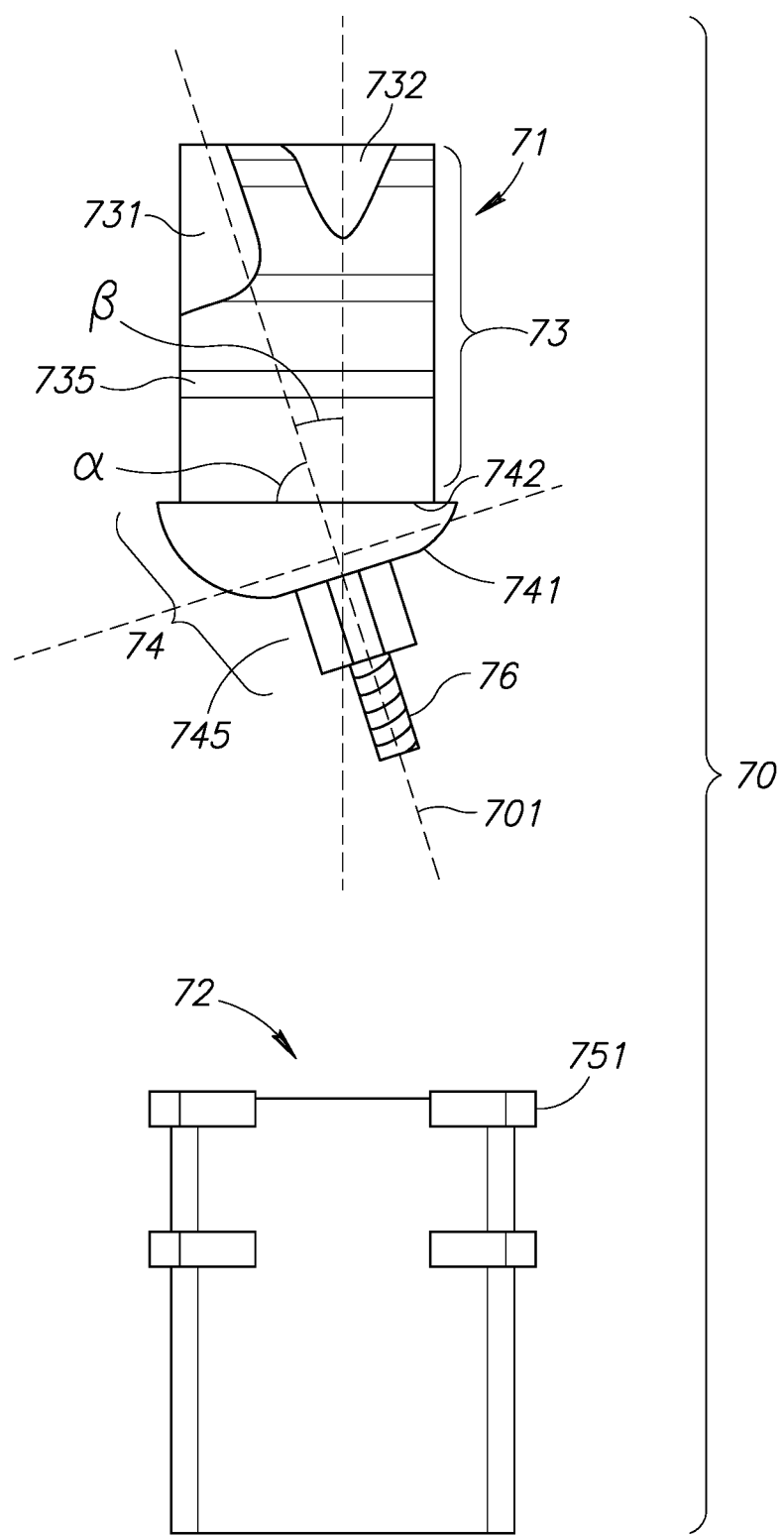
FIGS. 7A, 7B, 7C and 7D are schematic illustrations of an angulated transfer constructed and operative in accordance with a preferred embodiment of the present invention.
Figure 7B:
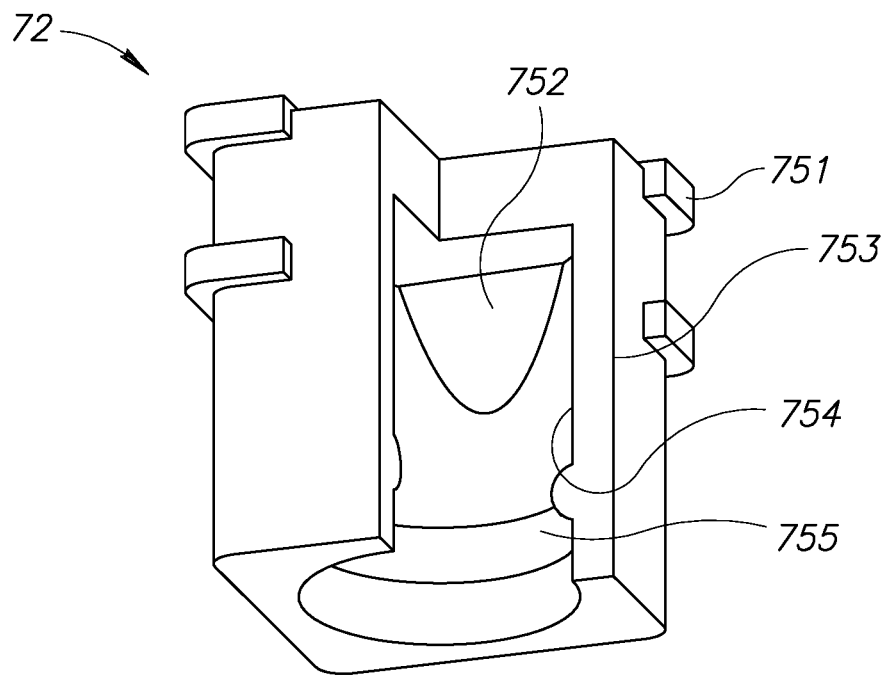
Figure 7C:
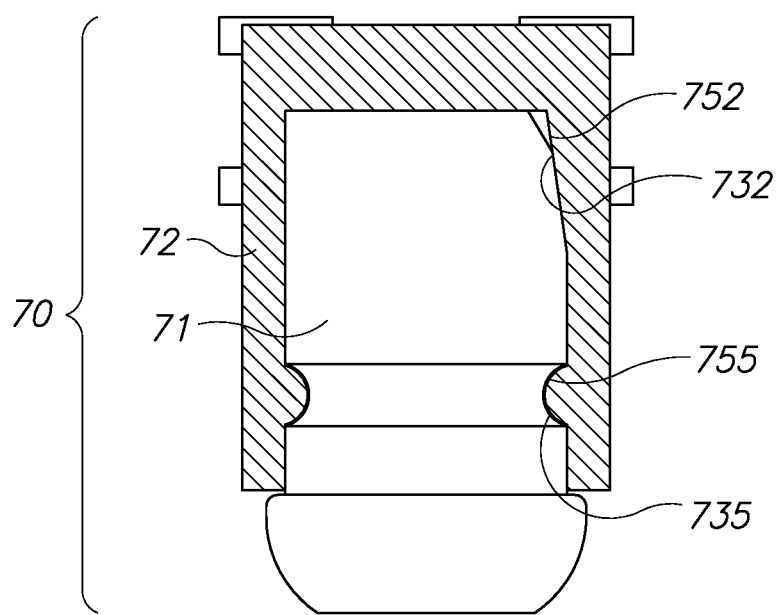
Figure 7D:
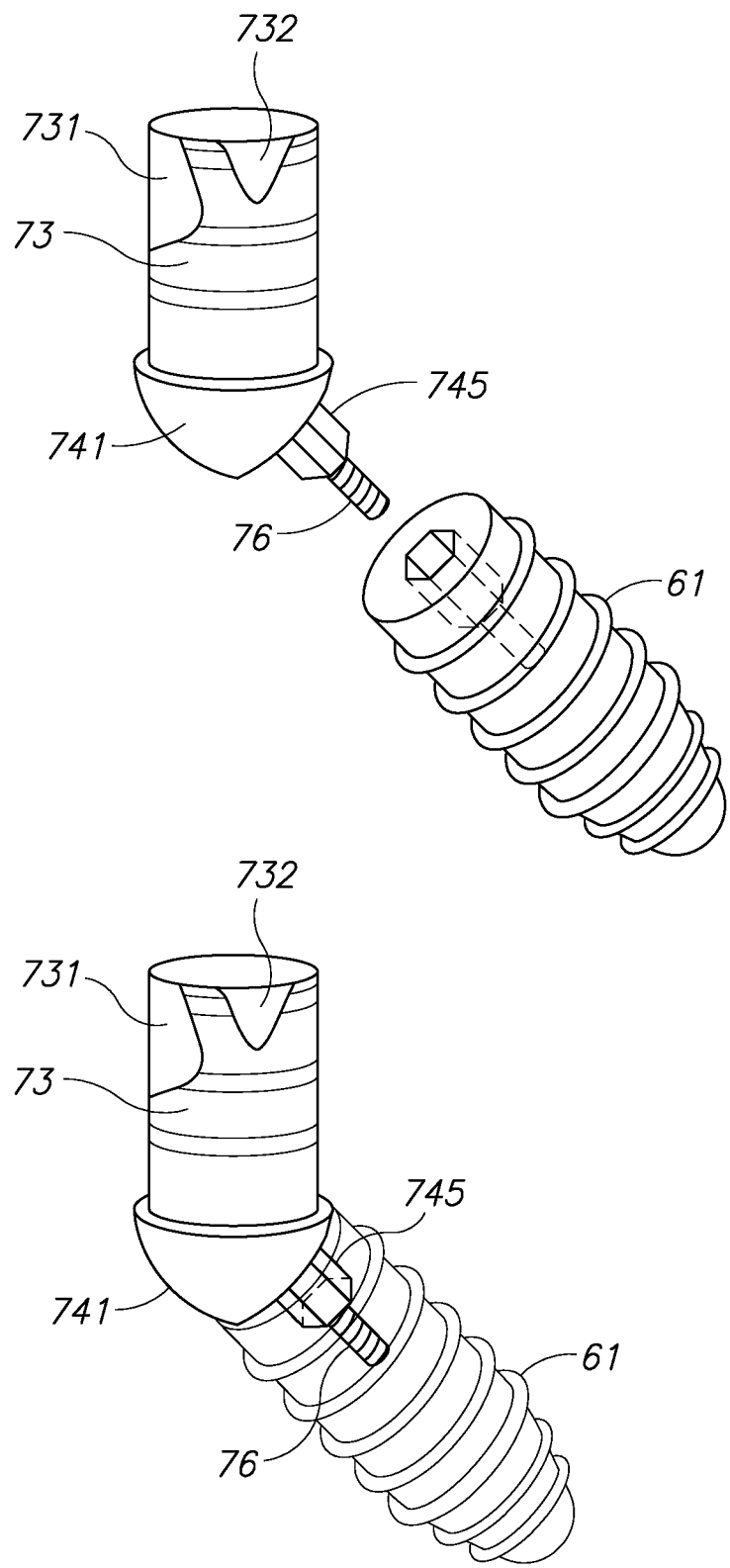

FIG. 7C shows plastic cap 72 snapped onto metal element 71. Anti-rotation protrusion 752 may be aligned with anti-rotation surface 732 and retention ridges 755 may be snapped into retention grooves 735. It may be appreciated that the anti-rotation element 732 may keep metal component 71 from being perfectly round such that plastic cap 72 may be aligned thereon in only one direction which thus may define the exact location of the implant.

It will be appreciated that protrusions 751 on outer surface 753 may stick more strongly into the elastomeric material than the snapped connection between plastic cap 72 to metal element 71 and thus may be easily released when pulled out (for example, when impression tray 22 is released).

Figure 8:
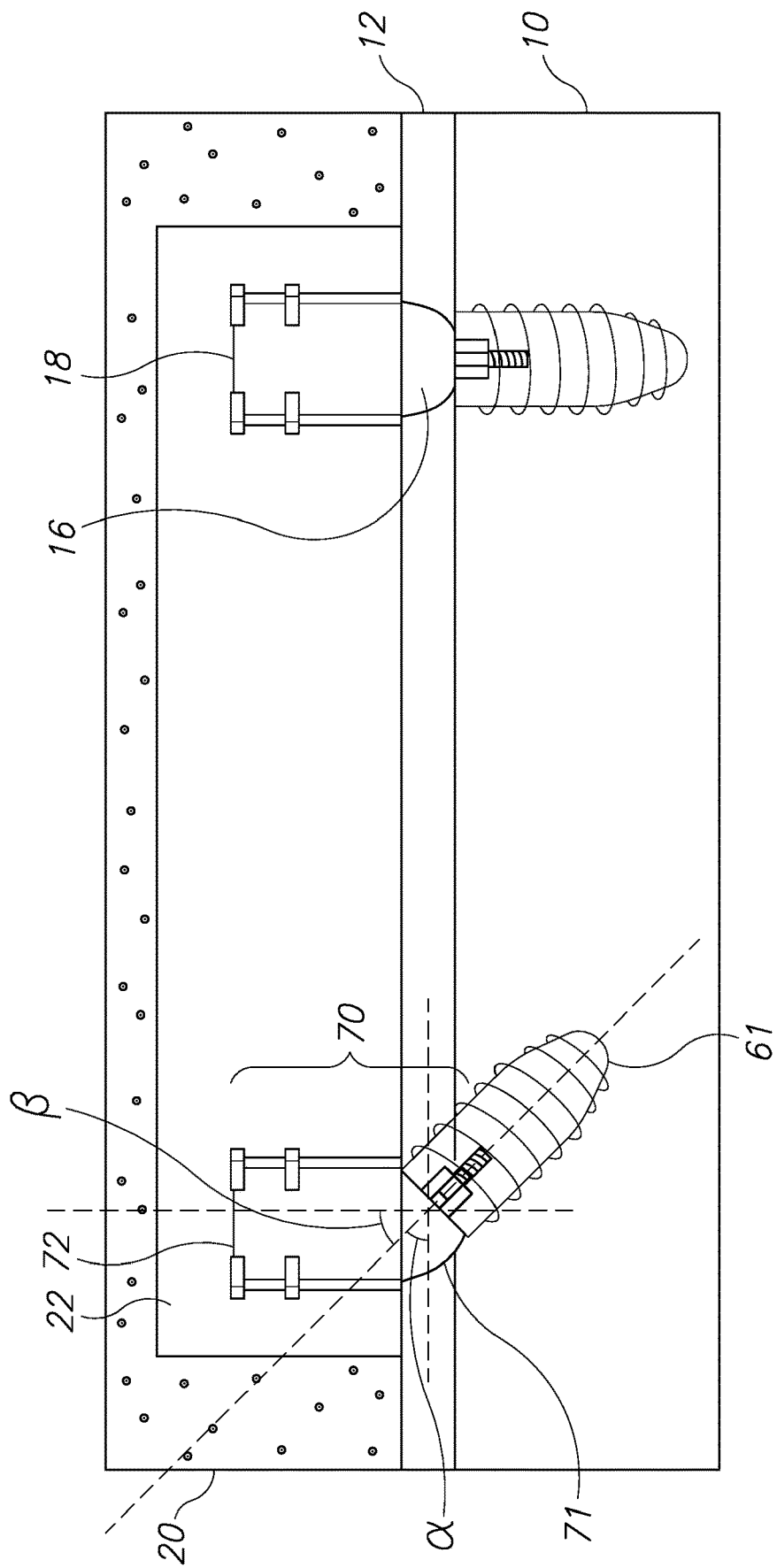
FIGS. 8, 9 and 10 are schematic illustrations of the procedure of transferring the location, angulation and timing of tilted implants.
Figure 9:
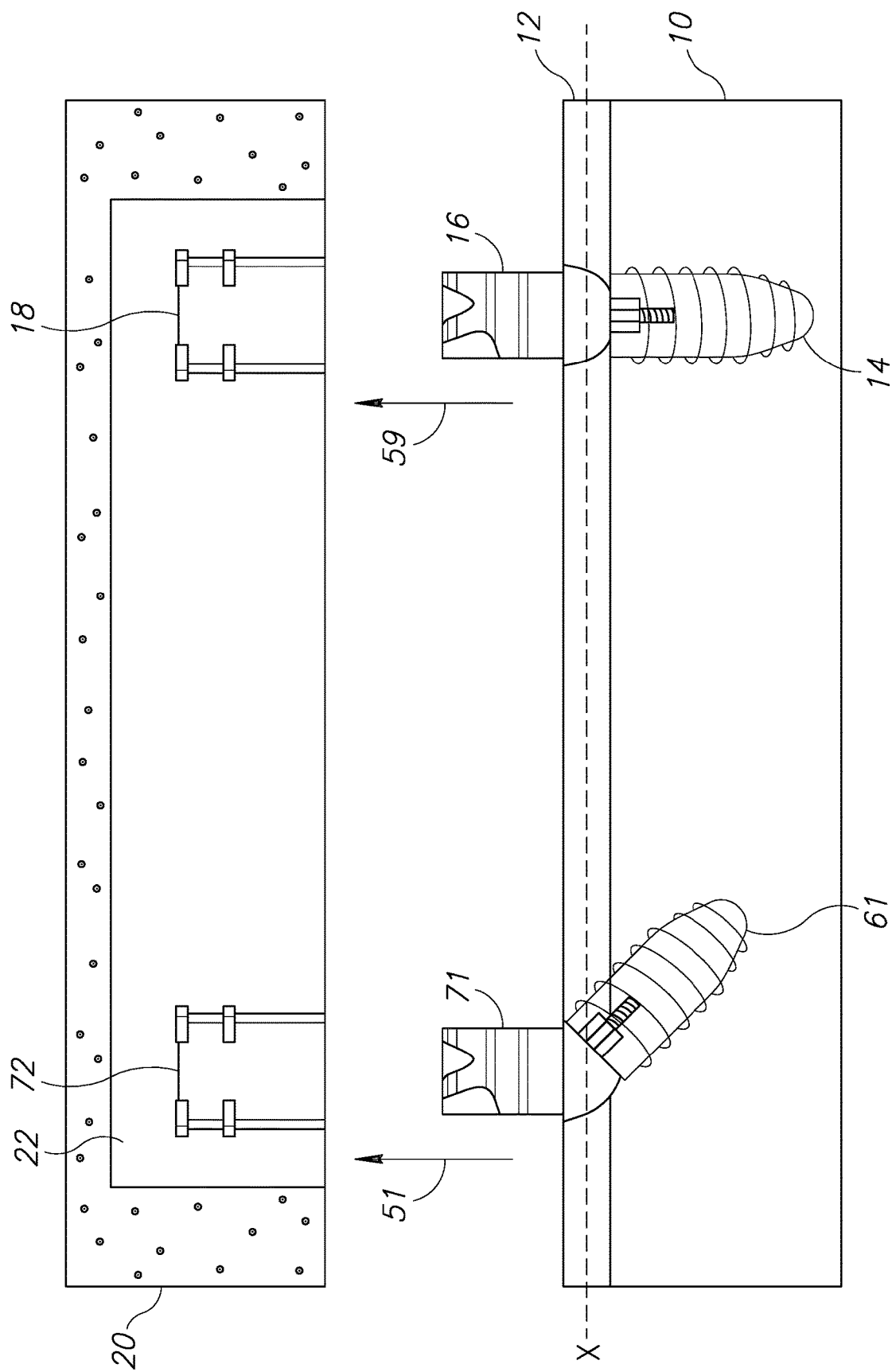
Figure 10:
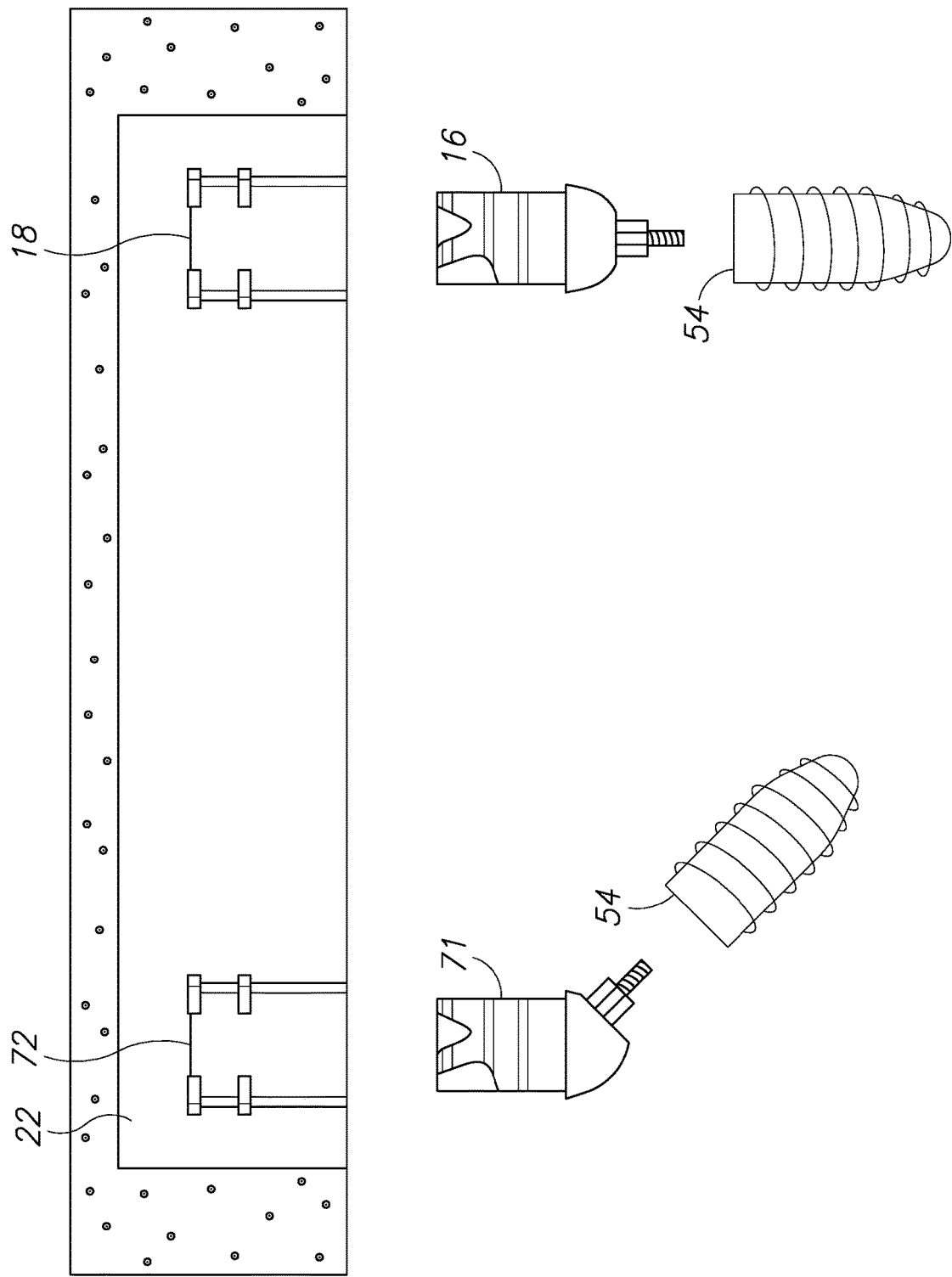

FIGS. 8-10 illustrate the use of angulated transfer 70 for creating a generally precise plaster model of tilted dental implants. Metal component 71 of angulated transfer 70 may have an angle β, and may correct the angulation of implant 61 relative to the release path of the impression. The result (FIG. 9), after hardening of impression material 22, may be a straight release path 51 for plastic cap 72, similar to the straight release path 59 for plastic cap 18 of straight implant 14. As both plastic caps 18 and 72 are perpendicular to occlusal plane x, they are both released easily from metal components 16 and 71 respectively, to which they both were connected.

It may be appreciated that the orientation of both plastic cap 18 and plastic cap 72, with respect to occlusal plane x, create parallel, vertical release paths, even though they represent straight implant 14 and tilted implant 61, respectively.

Plastic cap 72 may be released from metal component 71 similarly and with the same ease as plastic cap 18 from metal component 16 so the location and angulation accuracy of both plastic caps 72 and 18, is high even though they replicate angulated and straight implants respectively.

Figure 5:
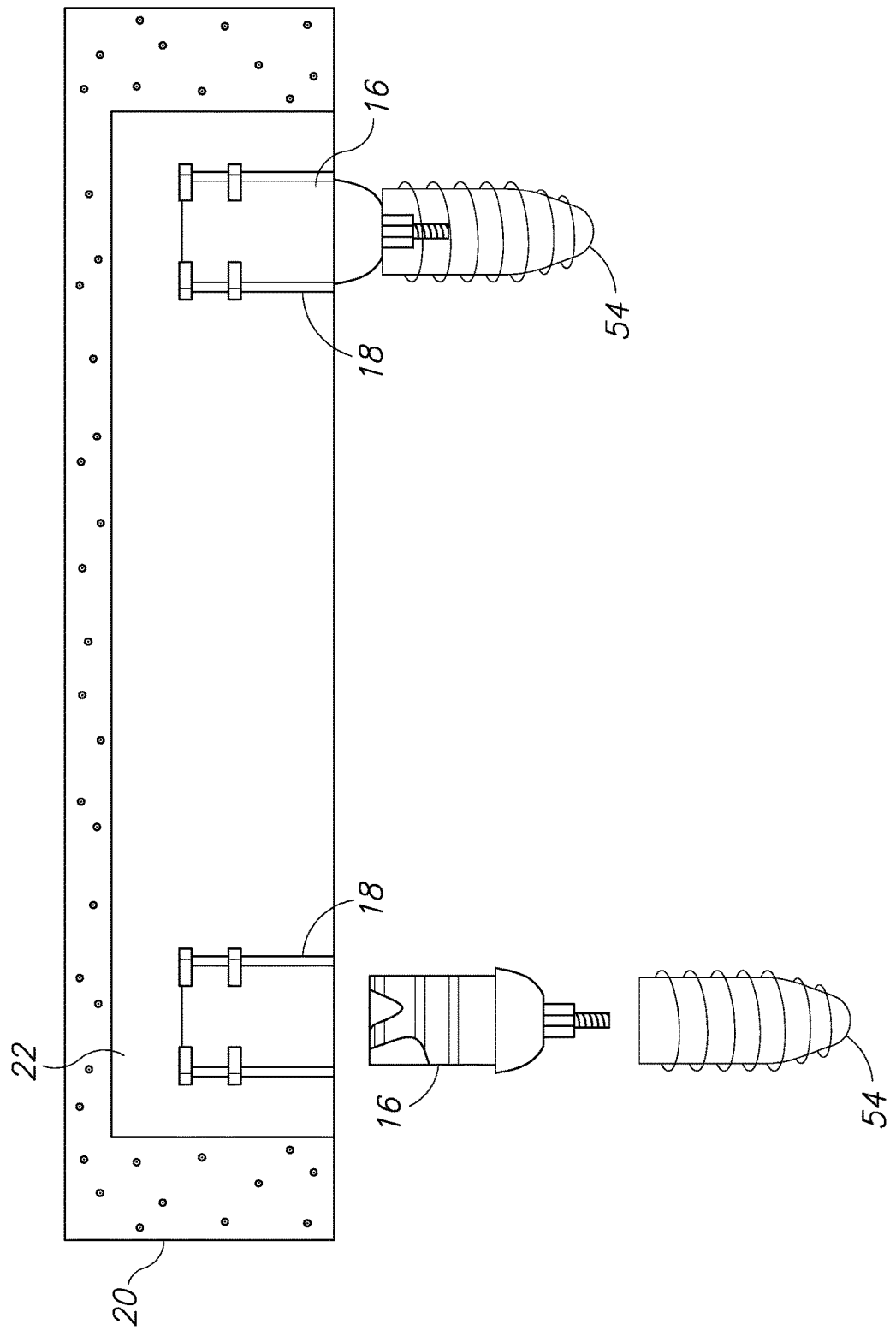

FIG. 10, to which reference is now briefly made, illustrates the procedure that takes place after impression material 22 is released from the mouth. This procedure is similar to the procedure described with respect to FIG. 5 hereinabove.

Metal component 71 may be removed from tilted dental implant 61 and screwed to implant analog 54. The resultant structure, built of removed metal component 71 and implant analog 54, may be snapped into plastic cap 72 immersed in impression material 22. Similarly, (as described in FIG. 5), metal component 16 may be removed from dental implant 14, screwed into implant analogs 54. The resultant structure, built of removed metal component 16 and implant analog 54, may be snapped into plastic cap 18 immersed in impression material 22 and may be used, all together, for standard fabrication of a dental plaster model in the dental laboratory.

It can be appreciated that using an angulated transfer with tilted implant in the closed tray technique, described hereinabove, may solve some of the problems of the prior art straight transfers when used with tilted implants and may provide a good replication of the angulated implant's three dimensional position, rotation and angulation.

It can also be appreciated that the angulated transfer apparatus may create a perpendicular release path to plastic caps used with angulated transfers, similar to the perpendicular release path of plastic caps used with straight transfers, resulting in parallel release paths for all plastic caps.

In addition, the angulated transfer may improve the impression taking technique for both patients and physicians. It may reduce the force needed to retrieve the impression tray from the dental arch with tilted implants and it may facilitate and shorten the work of creating the plaster model, by avoiding repeated, time consuming sessions. It may also shorten the clinical sessions and patient discomfort.

Moreover, usage of angulated transfer may improve the accuracy of implant location and angulation in the impression material, which may improve the quality of the plaster model, from which the prosthesis is created, and may result in production of better prosthesis.

Figure 11:
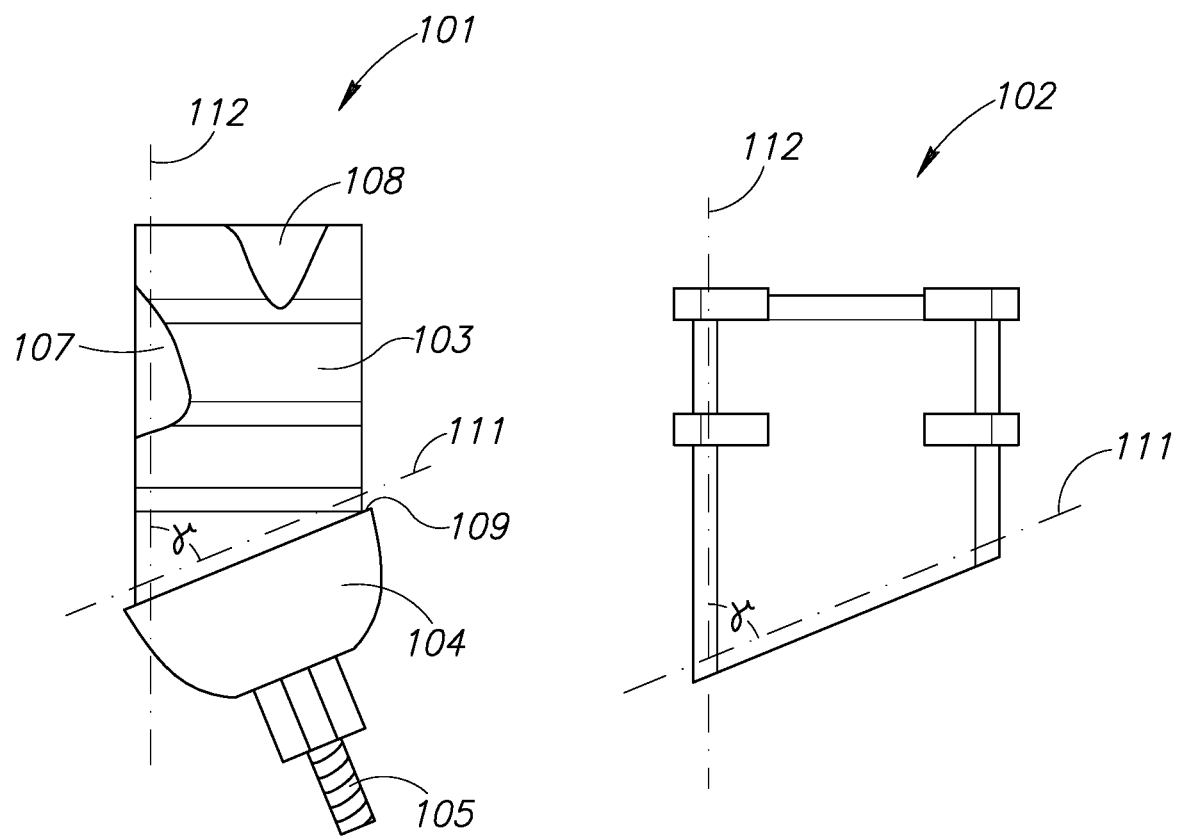
FIG. 11 is a schematic illustration of an alternative embodiment of an angulated transfer.

FIG. 11, to which reference is now made, illustrates an angulated transfer, constructed and operative according to an alternative embodiment of the present invention.

The angulated transfer of this embodiment comprises a metal component 101 and a plastic cap 102. Metal component 101 comprises a prosthesis placeholder 103, a screw 105 and a straight base 104.

Prosthesis placeholder 103, in the shape of a truncated cylinder, is truncated in an angle γ which is the angle between longitudinal axis 112 of prosthesis placeholder 103 and an axis 111 which is perpendicular to the implant.

The value of angle γ may be any value between 45° and 80°, for example, 75°, 65°, 60° or 45°, but may be fabricated in any angle desired according to the tilt of the implant. A screw access hole 107 and an anti-rotation groove 108 also lie within prosthesis placeholder 103 and operate in a manner similar to prosthesis placeholder 73.

In an alternative embodiment the angle of the angulated transfer may be set dynamically as needed according to the tilt of the implant. The angle may be set to different degrees using a special design including a calibration joint for adjusting the angle of the transfer to any tilted implant.

Plastic cap 102, in the shape of a truncated cylinder, may be truncated with the same angle γ as the angle of the applicable prosthesis placeholder 103. Plastic cap 102 operates similarly to plastic cap 72 of angulated transfer 70.

The angulated transfers may be made with different values of angle γ, so that a dentist may select the appropriate one according to the angulation of the dental implants in a patient mouth and the state of the patient's mouth.

It may be appreciated that the metal component may be fabricated from any suitable material such as porcelain and not necessarily from metal. In addition plastic cap can also be fabricated from any other suitable material.

It may be appreciated that the materials from which the components are fabricated, together or apart, may be of any suitable material. In addition the morphological design of both components together or apart, as well as their sizes, their height and their width, may be of any suitable morphological design and size height and width.

It may be appreciated that prosthesis placeholder 103 may be of any shape such as a cylindrical, elliptical, oval structure or the like, and may not need an anti-rotation grooves to maintain the rotation. It may also be appreciated that the rotation may be retained by grooves for symmetrical structures or by the asymmetry of prosthesis placeholder 103 when its structure is asymmetry.

It may also be appreciated that the method of adaptation between the prosthesis placeholder and the implant may be any suitable method and the adaptation may be a partial adaptation or complete coverage. Similarly, the type of the connection between the transfer and the implant may be of any suitable type, such as screwed or mechanically pressed to create a friction or any combination thereof.

It may be appreciated that the method of adaptation between the prosthesis placeholder and the plastic cap may be any method including a method that uses one or more retention grooves. The location of any retention groove, if exists, may be at any part of the metal component including the prosthesis placeholder and the base, and it can be also placed between the metal and plastic components.

It may also be appreciated that the shape, design and size of any part of the transfer, including the element connecting the transfer to the implant may be of any suitable shape design and size, and that the embodiments described herein are only exemplary embodiments of one possible option.

It may also be appreciated that the model may be fabricated from plaster, as described hereinabove however any material that may be used for creating the model such poly-urethane, epoxy or any other material may be used with the current invention.

While one embodiment of the metal component of present invention comprises three parts, other embodiments with more or less parts may be appropriate.

Other embodiments of the present invention that comprise an adaptation between two components, one provisionally or permanently fixed in the mouth and the other is snapped onto it and retrieved by the impression material and capable of transferring the implant location, rotation (timing) and tilt from the mouth may be implemented.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A system for transferring information about a tilted dental implant into an impression material, the system comprising:
   a cylindrical prosthesis placeholder having a single rotational fitting shape to provide a single spatial connection direction;
   a connector to connect said prosthesis placeholder to a tilted dental implant, said connector having a multi-sided cross-section to match a multi-sided connection opening of said dental implant;
   a wedged base coupling said connector to said prosthesis placeholder, said base comprising:
   an upper platform to be aligned to an occlusal plane; and
   a wedge having an angle similar to a tilt angle of said tilted dental implant with respect to a perpendicular axis of said occlusal plane; and
   a cap snappable onto said prosthesis placeholder in said single spatial connection direction, said cap comprising a bottom surface matching said upper platform,
   wherein said cap is releasable along said perpendicular axis and provides at least an indication of a rotation of said implant around its longitudinal axis and of a single rotation location of said implant around said perpendicular axis.

2. The system of claim 1, wherein said connector has the shape of an equilateral polygon.

3. The system of claim 1, wherein said connector comprises a screw.

4. The system of claim 1, wherein said angulated component is one of: a permanent prosthetic element and a temporary prosthetic element.

5. A system for transferring information about a tilted dental implant into an impression, the system comprising:
- a prosthesis placeholder having a single rotational fitting shape to provide a single spatial connection direction and formed as a cylinder truncated at an angle similar to a tilt angle of a tilted dental implant with respect to a perpendicular axis of an occlusal plane;
- a connector to connect said prosthesis placeholder to said tilted dental implant, said connector having a multi-sided cross-section to match a multi-sided connection opening of said dental implant;
- a base coupling said connector to said prosthesis placeholder, said base comprising an upper platform perpendicular to a longitudinal axis of said dental implant; and
- a cap snappable onto said prosthesis placeholder in said single spatial connection direction, said cap comprising an angled bottom surface matching said upper platform,
- wherein said cap is releasable along said perpendicular axis and provides at least an indication of a rotation of said implant around its longitudinal axis and of a single rotation location of said implant around said perpendicular axis.

6. The system of claim 5, wherein said system comprises a calibration joint for adjusting the angle of the transfer to any tilted implant.

7. The system of claim 5, wherein said connector has the shape of an equilateral polygon.

8. The system of claim 5, wherein said connector comprises a screw.

* * * * *